United States Patent
Kim et al.

(10) Patent No.: US 11,759,430 B2
(45) Date of Patent: Sep. 19, 2023

(54) ACTIVE SUBSTANCE CARRIER COMPRISING BIOPOLYMER

(71) Applicant: AMOREPACIFIC CORPORATION, Seoul (KR)

(72) Inventors: Eunmi Kim, Yongin-si (KR); Il Hong Bae, Yongin-si (KR); Jaewon You, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 158 days.

(21) Appl. No.: 17/109,931

(22) Filed: Dec. 2, 2020

(65) Prior Publication Data

US 2021/0161830 A1    Jun. 3, 2021

(30) Foreign Application Priority Data

Dec. 3, 2019    (KR) .................. 10-2019-0159034

(51) Int. Cl.
| | | |
|---|---|---|
| *A61K 9/51* | (2006.01) | |
| *A61K 9/48* | (2006.01) | |
| *A61K 9/00* | (2006.01) | |
| *A61K 8/02* | (2006.01) | |

(Continued)

(52) U.S. Cl.
CPC .......... *A61K 9/5169* (2013.01); *A61K 8/0279* (2013.01); *A61K 8/645* (2013.01); *A61K 8/73* (2013.01); *A61K 9/0014* (2013.01); *A61K 9/4816* (2013.01); *A61K 9/4891* (2013.01)

(58) Field of Classification Search
CPC ........ A61K 8/0279; A61K 8/645; A61K 8/73; A61K 9/4816; A61K 9/0014; A61K 9/4891; A61K 9/5161; A61K 9/5169; A61K 2800/10; A61K 2800/91; A61K 2800/412; A61K 2800/5922; A61Q 19/00
See application file for complete search history.

(56) References Cited

U.S. PATENT DOCUMENTS

| | | |
|---|---|---|
| 8,658,200 B2 | 2/2014 | Mody et al. |
| 2006/0147542 A1 | 7/2006 | Ono et al. |
| 2007/0110799 A1 | 5/2007 | Leferve et al. |

(Continued)

FOREIGN PATENT DOCUMENTS

| | | |
|---|---|---|
| CN | 103957893 A | 7/2014 |
| CN | 106692978 A | 5/2017 |

(Continued)

OTHER PUBLICATIONS

Liposomes: http://www.nanovec.com/en/liposomes/.*

(Continued)

*Primary Examiner* — Hong Yu
(74) *Attorney, Agent, or Firm* — Merchant & Gould P.C.

(57) ABSTRACT

The present disclosure relates to an active substance carrier comprising a core-shell network structure formed using a biopolymer. In an aspect of the present disclosure, the core-shell network structure comprises a core-shell particle comprising: a core comprising prolamin; and a shell comprising pullulan and pectin, wherein the pullulan comprised in the shell surrounds the core and the pectin is located in the outermost layer of the shell, so that a network is formed between the core-shell particles. It can effectively facilitate the transdermal absorption of an active substance.

3 Claims, 7 Drawing Sheets

Schematic of core-shell network structure

| Core | | Shell network | |
|---|---|---|---|
| Active substance | Prolamin | Pullulan | Pectin |

(51) Int. Cl.
*A61K 8/73* (2006.01)
*A61K 8/64* (2006.01)

(56) References Cited

U.S. PATENT DOCUMENTS

| | | |
|---|---|---|
| 2015/0342896 A1 | 12/2015 | Koyakutty et al. |
| 2017/0119803 A1 | 5/2017 | Koyakutty et al. |
| 2017/0333365 A1 | 11/2017 | Koyakutty et al. |
| 2019/0336931 A1* | 11/2019 | Lagaron Cabello ............ A61K 9/5042 |
| 2021/0393489 A1 | 12/2021 | Kim et al. |

FOREIGN PATENT DOCUMENTS

| | | |
|---|---|---|
| CN | 112891244 A | 6/2021 |
| EP | 2292102 A | 3/2011 |
| EP | 2591772 A1 | 5/2013 |
| JP | 09-252744 A | 9/1997 |
| JP | 2015-518370 A | 7/2015 |
| KR | 10-2003-0070799 A | 9/2003 |
| KR | 10-2005-0042873 A | 5/2005 |
| KR | 10-0648535 B1 | 11/2006 |
| KR | 10-2007-0091680 A | 9/2007 |
| KR | 10-2014-0041453 A | 4/2014 |
| KR | 1020140091054 A | 7/2014 |
| KR | 10-2017-0080671 A | 7/2017 |
| WO | 2005/060944 A1 | 7/2005 |
| WO | 2012-116282 A2 | 8/2012 |
| WO | 2013/068478 A1 | 5/2013 |
| WO | 2013/141964 A1 | 9/2013 |
| WO | 2014/197640 A1 | 12/2014 |
| WO | 2016/071466 A1 | 5/2016 |

OTHER PUBLICATIONS

Luo et al.: Zein-Based Micro- and Nano-Particles for Drug and Nutrient Delivery: A Review, https://onlinelibrary.wiley.com/doi/epdf/10.1002/app.40696. (Year: 2014).*

Huang et al.: Encapsulation of resveratrol in zein/pectin core-shell nanoparticles: Stability, bioaccessibility, and antioxidant capacity after simulated gastrointestinal digestion, Food Hydrocolloids, 2019, 93, 261-269 (Year: 2019).*

Hu et al.: Core-shell biopolymer nanoparticle delivery systems: Synthesis and characterization of curcumin fortified zein-pectin nanoparticles, Food Chemistry, 2015, 182, 275-281. (Year: 2015).*

Zhang et al.: Core-shell biopolymer nanoparticle delivery systems: Synthesis and characterization of curcumin fortified zein-pectin nanoparticles, Food Chemistry, 2014, 142, 269 (Year: 2014).*

Dhanya At et al., "Development of Zein-Pectin Nanoparticle as Drug carrier", International Journal of Drug Delivery, vol. 4: 147-152 (2012).

K. Hu et al., "Core-shell biopolymer nanoparticle delivery systems: Synthesis and characterization of curcumin fortified zein-pectin nanoparticles", Food Chemistry, vol. 182: 275-281 (2015).

Z.K. Mukhidinov et al., "Pectin-Zein Microspheres as Drug Delivery Systems", Pharmaceutical Chemistry Journal, vol. 44, No. 10: 564-567 (2011).

SC Liu et al., "Electrospun Food-Grade Ultrafine Fibers from Pectin and Pullulan Blends", Food and Nutrition Sciences, vol. 7: 636-646 (2016).

MZ. Trevino-Garza et al., "Edible Active Coatings Based on Pectin, Pullulan, and Chitosan Increase Quality and Shelf Life of Strawberries (*Fragaria ananassa*)", Journal of Food Science, vol. 80, No. 8: M1823-M1830 (2015).

Xulin et al., "Study on the preparation and biological activity of curcumin loaded zein/polysaccharide nanoparticles", Journal of Guangdong Pharmaceutical University, 2016, vol. 32, No. 5, pp. 545-549.

Liu et al., "Pectin/Zein Beads for Potential Colon-Specific Drug Delivery: Synthesis and in Vitro Evaluation", Drug Delivery, 2006, vol. 13, No. 6, pp. 417-423.

Office Action for Chinese Application No. 201980072732.2 (dated Jan. 13, 2022).

* cited by examiner

US 11,759,430 B2

ACTIVE SUBSTANCE CARRIER COMPRISING BIOPOLYMER

TECHNICAL FIELD

The present disclosure relates to an active substance carrier using a biopolymer.

CROSS-REFERENCE TO RELATED APPLICATION

This application claims the priority of Korean Patent Application No. 10-2019-0159034, filed on Dec. 3, 2019, and all the benefits accruing therefrom under 35 U.S.C. § 119, the contents of which in their entirety are herein incorporated by reference.

BACKGROUND ART

In the cosmetics industry or pharmaceutical industry, formulations for external application to skin comprising active substances that cannot easily penetrate into the stratum corneum use synthetic surfactants, etc. in order to promote absorption of the active substances into the skin. Optionally, polymer nanoparticles using synthetic polymers such as polyethylene glycol or liposome nanoparticles have been widely used as carriers for increasing the skin penetrability of active substances. For example, low-molecular-weight polar solvents such as ethanol, propylene glycol, dimethyl sulfoxide or amphiphilic compounds are used together, or fatty acids having polar head groups and hydrophobic chains, alcohols, 1-dodecylazepan-2-one (Azone), 2-nonyl-1,3-dioxolane (SEPA 009), dodecyl-2-dimethylaminopropionate (DDAIP), etc. have been used. However, since the amphiphilicity enhancers are synthetic compounds or organic solvents are used for their preparation, there are safety issues such as in-vivo toxicity or allergenicity. Recently, their use is avoided in the cosmetics industry and the pharmaceutical industry.

Accordingly, development of a carrier which is friendly to the human body and environment and can effectively enhance the transdermal absorption of active substances is need.

DISCLOSURE

Technical Problem

In an aspect, the present disclosure is directed to providing a carrier which is biocompatible by using a biopolymer and is capable of facilitating the transdermal absorption of an active substance.

Technical Solution

In an aspect, the present disclosure provides an active substance carrier comprising a core-shell network structure comprising a core-shell particle consisting of a core comprising prolamin; and a shell comprising pullulan and pectin, wherein the pullulan comprised in the shell surrounds the core and the pectin is located in the outermost layer of the shell, so that a network is formed between the core-shell particles.

In an aspect, the present disclosure provides a composition for external application to skin, which comprises an active substance and an active substance carrier comprising the core-shell network structure.

Advantageous Effects

In an aspect, the present disclosure can facilitate the transdermal absorption of an active substance with a core-shell network structure formed using a biocompatible biopolymer. The core-shell network structure of the present disclosure allows effective absorption of an active substance into skin by supporting an active substance with low penetrability into the stratum corneum and delivering the same to the stratum granulosum through the stratum corneum. Therefore, the present disclosure can solve the safety issue related with the use of the existing synthetic chemicals and can enhance the effect of a cosmetic composition or a pharmaceutical composition comprising an active substance by allowing the active substance to be effectively absorbed into the skin.

BEST MODE

Figure 1:
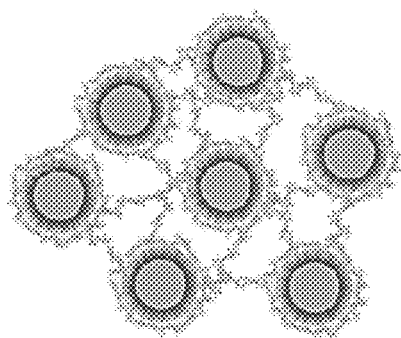
FIG. 1 schematically shows a core-shell network structure comprised in a composition according to an exemplary embodiment of the present disclosure.

Hereinafter, exemplary embodiments of the present application will be described in detail referring to the attached drawings. However, the technology disclosed in this application is not limited to the exemplary embodiments described herein but may be embodied in other forms. The exemplary embodiments described herein are provided so that the disclosure is through and complete and the idea of this application is fully conveyed to those skilled in the art. In the drawings, the dimensions of some elements, such as width, thickness, etc., are somewhat exaggerated for more clear description. In addition, although some elements are illustrated only in part, those skilled in the art will easily understand the remaining part of the elements. In addition, those of ordinary skill in the art will be able to embody the present application in various other forms within the scope not departing from the technical idea of the present application.

FIG. 1 shows an exemplary embodiment of the present disclosure. Referring to FIG. 1, an exemplary embodiment of the present disclosure is a core-shell network structure formed using biopolymers, wherein the core may comprise prolamin and the shell may comprise pullulan and pectin. The pullulan surrounds the core and the pectin is located in the outermost layer of the shell, so that a network is formed between the core-shell particles.

In the present disclosure, a core-shell network structure wherein a network is formed between the core-shell particles is named "ECOWEB".

In the present disclosure, the term "biopolymer" is contrasted with "synthetic polymer". The biopolymer is a polymer material constituting or produced by an organism and the term is used in the broadest concept, comprising nucleic acids, polysaccharides, proteins, etc.

In an exemplary embodiment, the present disclosure may provide an active substance carrier comprising the core-shell network structure.

In an exemplary embodiment, the present disclosure may provide an active substance carrier comprising the core-shell network structure, as a carrier for facilitating the transdermal absorption of an active substance.

In an exemplary embodiment, the present disclosure may provide a composition for external application to skin, which comprises an active substance and an active substance carrier comprising the core-shell network structure.

In another exemplary embodiment, the present disclosure may provide a use of the active substance carrier comprising the core-shell network structure for use in preparation of a composition for external application to skin, which comprises an active substance. In another exemplary embodiment, the present disclosure may provide a method for transdermal delivery of an active substance, which comprises administering an effective amount of the active substance carrier carrying the active substance to a subject in need thereof. In another exemplary embodiment, the present disclosure may provide the core-shell network structure as an active substance carrier for facilitating the transdermal absorption of an active substance of a composition for external application to skin, which comprises the active substance. In addition, the present disclosure may provide a use of the core-shell network structure as a carrier of an active substance.

In the present disclosure, the prolamin is a simple plant storage protein rich in glutamine and proline. It has self-assembled hydrophobic amino acids such as leucine, isoleucine, etc. distributed on the surface. Accordingly, the prolamin can effectively encapsulate an active substance by forming a brick-like stacked structure such as nanorods around the active substance. In an exemplary embodiment, the prolamin may comprise one or more selected from a group consisting of zein, hordein, secalin, kafirin, gliadin, oryzin and avenin. However, any material belonging to the prolamin family may be used without being limited thereto. Specifically, zein may be isolated or extracted from corn, hordein from barley, secalin from rye, kafirin from millet, gliadin from wheat, oryzin from rice, and avenin from oats.

In an exemplary embodiment, the structure may comprise 0.001-7.5 wt % of prolamin based on the total weight of the core-shell network structure. In addition, in an exemplary embodiment, the prolamin may be comprised in an amount of 0.01-3 wt % based on the total weight of a composition comprising the active substance. The prolamin serves as a core of a Pickering emulsion through hydrophobic interaction with the active substance. If the content exceeds the upper limit described above, the active substance and prolamin are dispersed in the network structure, forming a large aggregated precipitate, instead of a plurality of core-shell particles. As a result, the core-shell network structure is not formed and the composition itself may be separated into a poorly soluble phase and a soluble phase. Specifically, the prolamin may be comprised in an amount of 0.001 wt % or more, 0.005 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more or 3 wt % or more, based on the total weight of the composition. In an exemplary embodiment, the prolamin may be comprised in an amount of 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In the present disclosure, the pullulan is a substance obtained from the black, yeast-like fungus *Aureobasidium*

*pullulans* by isolating and purifying polysaccharides. It may comprise the trisaccharide maltotriose, which consists of three glucose units connected by α-1,4 glycosidic linkage. Being hydrophilic, it dissolves well in water but not in alcohols. With coating and adhesive properties, it can be coated on the core comprising the prolamin, thereby forming a core-shell structure.

In an exemplary embodiment, the structure may comprise the pullulan in an amount of 0.001-12.5 wt % based on the total weight of the core-shell network structure. In addition, in an exemplary embodiment, the pullulan may be comprised in an amount of 0.01-5 wt % based on the total weight of a composition comprising the active substance. When the content of the pullulan is within the above-described range, a coat may be formed effectively on the core and the stability of the composition can be improved. If the content of the pullulan is lower than 0.001 wt %, the core-shell structure is not formed effectively in the composition and the active substance may be precipitated as the structure is dissociated. Specifically, the pullulan may be comprise in an amount of 0.001 wt % or more, 0.005 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more or 5 wt %, based on the total weight of the composition. In an exemplary embodiment, the pullulan may be comprise in an amount of 5 wt % or less, 4 wt % or less, 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In the present disclosure, the pectin is a hydrated gel surrounding the cellulose-hemicellulose network in a plant and is a polysaccharide whose main component is galacturonic acid, an oxide of galactose. When the core-shell structure consists only of prolamin and pullulan and the active substance is loaded in a minimum amount or more, if the content of the active substance is increased, the core-shell structure may be precipitated due to increased weight. In addition, when applied onto skin by applying to a composition in the form of an emulsion or an oil-in-water (O/W) emulsion, the active substance cannot be delivered effectively below the stratum corneum of the skin due to aggregation induced by hydrophobic interaction. That is to say, the active substance in the composition may be separated rather than being dispersed, forming large particles of micrometer or larger scales, and transdermal absorption is not achieved effectively. In contrast, in an exemplary embodiment of the present disclosure, as the pectin is comprised in the shell, a structure wherein core-shell particles are interconnected is formed, the core-shell particles are maintained stably, and the degree of precipitation can be minimized. In addition, the active substance may remain dispersed uniformly in the composition due to repulsion between the negatively charged core-shell particles. Because the core-shell particles encapsulating the active substance are present in the aqueous phase of the composition in the form of nanosized droplets, the active substance can be delivered effectively below the stratum corneum of the skin when applied to the skin.

In an exemplary embodiment, the structure may comprise the pectin in an amount of 0.001-10 wt % based on the total weight of the core-shell network structure. In addition, in an exemplary embodiment, the pectin may be comprised in an amount of 0.01-2 wt % based on the total weight of the composition comprising the active substance. If the content of the pectin is within the above-described, a physically stabilized structure may be obtained as a network supporting the core-shell particles is formed effectively and the transdermal penetration of the active substance may be facilitated. If the content of the pectin is less than 0.001 wt %, the composition may be separated and the active substance may be precipitated because a network supporting the core-shell particles is not formed stably.

Specifically, the pectin may be comprised in an amount of 0.001 wt % or more, 0.005 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more or 2 wt %, based on the total weight of the composition. In an exemplary embodiment, the pectin may be comprised in an amount of 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In an exemplary embodiment, the core-shell particle may have an average particle size which is greater than 100 nm and equal to or smaller than 600 nm. The average particle size refers to the average of the largest diameter of the particles. The average particle size means the average size of at least 90% of core-shell particle distributed in the structure, carrier or composition. Specifically, the average particle size may mean the average of the largest diameter of at least 90% or more, 91% or more, 92% or more, 93% or more, 94% or more, 95% or more, 96% or more, 97% or more, 98% or more or 99% or more of droplet particles distributed in the structure, carrier or composition. In the present disclosure, the hydrophobic core is coated with the hydrophilic polysaccharide comprising pullulan and pectin and the core-shell particles are densely interconnected with each other. Thus, the composition comprising the core-shell network structure can stably maintain a structure wherein particles with an average particle size of greater than 100 nm and equal to or smaller than 600 nm are distributed uniformly for a long time without precipitation, and can function as a carrier which delivers the active substance effectively below the stratum corneum of the skin. Specifically, the average particle size of the core-shell particle may be 101 nm or greater, 150 nm or greater, 200 nm or greater, 250 nm or greater, 300 nm or greater, 350 nm or greater, 400 nm or greater, 450 nm or greater, 500 nm or greater or 550 nm or greater. Specifically, the average particle size of the core-shell particle may be 600 nm or smaller, 550 nm or smaller, 500 nm or smaller, 450 nm or smaller, 400 nm or smaller, 350 nm or smaller, 300 nm or smaller, 250 nm or smaller, 200 nm or smaller or 150 nm or smaller.

In an exemplary embodiment, the present disclosure may provide a composition for external application to skin, which comprises an active substance and an active substance carrier comprising the core-shell network structure described above, wherein the active substance is encapsulated in the prolamin of the core. In an exemplary embodiment, the active substance may be any substance having efficacy useful for the skin or body without limitation. In an exemplary embodiment, the active substance may be a water-insoluble or poorly water-soluble substance which is not easy to be delivered transdermally by itself. In an exemplary embodiment, the active substance may be hydrophilic or hydrophobic. In an exemplary embodiment, the active substance may be alcohol-soluble. In an exemplary embodiment, the active substance may comprise one or more of a plant-derived chemical and an animal-derived chemical. In an exemplary embodiment, the active substance may be a synthetic chemical. In the present disclosure, the plant-derived chemical, also called a "phytochemical", refers to a chemical compound comprised in a pant. Specifically, the active substance may comprise a saponin, a flavonoid, a lignan, a terpenoid or a mixture thereof, although not being limited thereto. For example, the saponin may comprise a ginsenoside. In an exemplary embodiment, the saponin may comprise ginsenoside Rg1, Rb1, Rg3, Rh2, Rf2, Rs1, Rb2, Rs2, Rs3 or Re, compound K (20-O-β-D-glucopyranosyl-20(S)-protopanaxadiol), etc., although not being limited thereto. In an exemplary embodiment, the terpenoid may comprise sterol, a steroid, a retinoid, a gibberellin, abscisic acid, a carotenoid, menaquinone, plastoquinone or ubiquinone. Alternatively, the terpenoid may comprise one or more triterpenoid selected from a group consisting of oleanolic acid, ursolic acid and arjunolic acid, although not being limited thereto. In an exemplary embodiment, the active substance may comprise one or more polyphenol or polyphenol derivative selected from a group consisting of amentoflavone, ellagic acid, apigenin, berginin, diosmetin, univestin, resveratrol, isoflavone and catechin, although not being limited thereto. In an exemplary embodiment, the active substance may comprise one or more oily fatty acid selected from a group consisting of salicylic acid, α-lipoic acid, caffeine, tocopherol, docosahexaenoic acid (DHA), eicosapentaenoic acid (EPA) and conjugated linoleic acid (CLA), although not being limited thereto. In an exemplary embodiment, the active substance may comprise one or more sphingolipid selected from a group consisting of sphingomyelin, ganglioside, cerebroside, ceramide, glycosyl ceramide, lactosyl ceramide, galactosyl ceramide and xylosyl ceramide, although not being limited thereto. In an exemplary embodiment, the active substance may comprise a carotene or a carotene derivative, although not being limited thereto. In an exemplary embodiment, the active substance may comprise one or more natural extract selected from a group consisting of ginkgo leaf extract and red ginseng extract, although not being limited thereto. In the present disclosure, the animal-derived chemical may comprise, for example, horse fat, mucin, etc.

In an exemplary embodiment, the active substance may be comprised in an amount of 0.01-10 wt % based on the total weight of the composition. If the content is below 0.01 wt %, the desired effect of the active substance may not be exerted sufficiently. In an exemplary embodiment, when the active substance is a single hydrophobic substance, if the content of the active substance exceeds 10 wt %, the formation of the core-shell particle may be inhibited and the active substance may be precipitated due to the hydrophobic interaction between the active substance and the prolamin. Additional thickening may be required to maintain the core-shell network structure. Specifically, the active substance may be comprised in an amount of 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more or 9.99 wt % or more, based on the total weight of the composition. In an exemplary embodiment, the active substance may be comprised in an amount of 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less or 0.01 wt % or less, based on the total weight of the composition.

In an exemplary embodiment, the weight ratio of the active substance carrier with respect to the total weight of the active substance may be 0.001-10:0.02-22.

In an exemplary embodiment, the present disclosure may provide a method for preparing the structure or an active substance carrier comprising the same. In an exemplary embodiment, the method may comprise: a step of forming a core by adding and dispersing prolamin in an alcohol solvent; a step of forming a shell surrounding the core by adding pullulan to the alcohol solution drop by drop; a step of coating pectin on an uppermost layer of the shell by adding pectin to the pullulan-added alcohol solution and forming a network between the shells; and a step of obtaining a solution with a core-shell network structure formed in an aqueous phase by evaporating the alcohol from the pectin-added solution.

In an exemplary embodiment, the present disclosure may provide a method for preparing a composition with an active substance loaded in the core-shell network structure. In an exemplary embodiment, the method may comprise: a step of forming a core by adding and dispersing prolamin and an active substance in an alcohol solvent; a step of forming a shell surrounding the core by adding pullulan to the alcohol solution drop by drop; a step of coating pectin on an uppermost layer of the shell by adding pectin to the pullulan-added alcohol solution and forming a network between the shells; and a step of obtaining a solution with a core-shell network structure formed in an aqueous phase by evaporating the alcohol from the pectin-added solution.

In an exemplary embodiment, the step of dispersing the prolamin and the active substance in the alcohol solvent may comprise adding the prolamin to the alcohol solvent, adding the active substance thereto and then dispersing the same.

The prolamin is a simple protein which is soluble in 60-90% alcohol. It is soluble in dilute alcohol, but not in water or an anhydrous alcohol solution. Accordingly, in an exemplary embodiment, the prolamin added to the alcohol solvent may be soluble in 60-90% alcohol. Also, in an exemplary embodiment, the alcohol solvent to which the active substance is added may be 70-95% alcohol. When the prolamin and the active substance are added to the alcohol as described above, a structure wherein the active substance is encapsulated by the prolamin may be formed due to the hydrophobic interaction between the active substance and the prolamin.

In an exemplary embodiment, the pullulan and the pectin added to the alcohol solution may be pullulan in aqueous phase and pectin in aqueous phase, respectively. Specifically, the pullulan in aqueous phase and the pectin in aqueous phase may be an aqueous pullulan solution and an aqueous pectin solution, more specifically 1-10% aqueous pullulan solution and aqueous pectin solution, respectively.

In an exemplary embodiment, phase separation occurs when the pullulan and the pectin are dissolved in an aqueous phase and then added to an alcohol solution wherein the prolamin or the prolamin and the active substance is/are dispersed. Due to the phase separation, the core comprising the prolamin or the prolamin and the active substance, which has been dispersed in the alcohol, is precipitated and, at the same time, a hydrophobic core is formed as a self-assembled layered structure of the prolamin is formed. A shell structure is formed as the pullulan is coated around the core, and a core-shell particle is formed as the pectin surrounds the uppermost layer. These particles are dispersed uniformly and stably in the alcohol solution, forming a Pickering emulsion. If the acidity of the solution is adjusted to pH 2.5-6.5, an interconnected network of core-shell particles is formed by the remaining alcohol. The composition according to an exemplary embodiment of the present disclosure can load an active substance at a high content because the network structure serves as a support of the core-shell structure, and the core-shell network structure can remain dispersed stably for a long time.

In an exemplary embodiment, the method may further comprise a step of gelating the solution wherein the core-shell network structure is formed by adjusting the acidity of the alcohol solution to pH 2.5-6.5. Pectin may be gelated in the presence of an acid or a sugar. The hydroxyl groups of a sugar forms hydrogen bonding with each other or forms ionic bonding with calcium ions. On the other hand, depolymerization occurs under basic or weakly acidic conditions. Alternatively, a gelated solution may be prepared when the content of the pectin is 2 wt % or more and 3 wt % or less based on the total weight of the composition as the viscosity of the solution itself is increased. The gelation is advantageous in that microbial contamination can be prevented due to osmosis.

In an exemplary embodiment, the temperature in the step of evaporating the alcohol is not limited as long as the solution wherein the core-shell network structure is dissolved in an aqueous phase can be obtained by evaporating the alcohol. For example, the temperature may be in the range of 20-70° C.

In an exemplary embodiment, the administration amount of the active substance carrier comprising the core-shell network structure or the composition comprising the same when applied to the skin may be 1 mg/kg/day to 1 g/kg/day. In an exemplary embodiment, the administration amount of the active substance carrier comprising the core-shell network structure or the composition comprising the same may be varied in consideration of the age, sex and body weight of a subject, the particular disease or pathological condition of the subject, the severity of the disease or pathological condition or administration route. The determination of the administration amount based on these factors is within the level of those skilled in the art. For example, the administration amount may be 1 mg/kg/day or more, 2 mg/kg/day or more, 3 mg/kg/day or more, 4 mg/kg/day or more, 5 mg/kg/day or more, 10 mg/kg/day or more, 20 mg/kg/day or more, 30 mg/kg/day or more, 40 mg/kg/day or more, 50 mg/kg/day or more, 60 mg/kg/day or more, 70 mg/kg/day or more, 80 mg/kg/day or more, 90 mg/kg/day or more, 100 mg/kg/day or more, 110 mg/kg/day or more, 120 mg/kg/day or more, 130 mg/kg/day or more, 140 mg/kg/day or more, 150 mg/kg/day or more, 160 mg/kg/day or more, 170 mg/kg/day or more, 180 mg/kg/day or more, 190 mg/kg/day or more, 200 mg/kg/day or more, 250 mg/kg/day or more, 300 mg/kg/day or more, 350 mg/kg/day or more, 400 mg/kg/day or more, 450 mg/kg/day or more or 500 mg/kg/day or more. In addition, the administration amount may be, for example, 1 g/kg/day or less, 500 mg/kg/day or less, 450 mg/kg/day or less, 400 mg/kg/day or less, 350 mg/kg/day or less, 300 mg/kg/day or less, 250 mg/kg/day or less, 200 mg/kg/day or less, 190 mg/kg/day or less, 180 mg/kg/day or less, 170 mg/kg/day or less, 160 mg/kg/day or less, 150 mg/kg/day or less, 140 mg/kg/day or less, 130 mg/kg/day or less, 120 mg/kg/day or less, 110 mg/kg/day or less or 100 mg/kg/day or less. However, the administration amount does not limit the scope of the present disclosure by any means.

The composition for external application to skin according to an exemplary embodiment of the present disclosure may be a cosmetic composition.

In an exemplary embodiment, the cosmetic composition according to the present disclosure may be formulated by comprising a cosmetologically or dermatologically acceptable medium or base. It can be provided as any formulation suitable to topical application, e.g., as a solution, a gel, a solid, an anhydrous paste, an oil-in-water emulsion, a suspension, a microemulsion, a microcapsule, a microgranule, an ionic (liposome) or non-ionic vesicular dispersion, a film, a cream, a skin lotion, a lotion, a powder, an ointment, a spray or a conceal stick. In addition, it can be used in the form of a foam or an aerosol composition which further comprises a compressed propellant. These compositions can be prepared by methods commonly employed in the art.

In an exemplary embodiment, the cosmetic composition according to the present disclosure may further comprise, in addition to the main ingredient, other ingredients that provide a synergistic effect to the main effect within the range not negatively affecting the main effect, and the ingredients other than the main ingredient may be selected and mixed without difficulty by those skilled in the art in consideration of the formulation of the cosmetic composition or purpose of use. In another exemplary embodiment the present disclosure, the cosmetic composition may further comprise, in addition to the main ingredient, other ingredients commonly comprised in cosmetic compositions. Examples may comprise a humectant, an emollient, an organic or inorganic pigment, an organic particle, a UV absorbent, an antiseptic, a sterilizer, an antioxidant, a plant extract, a pH control agent, an alcohol, a coloring agent, a fragrance, a blood circulation stimulant, a cooling agent, an antiperspirant, purified water, etc. However, the other ingredients that may be comprised in the cosmetic composition of the present disclosure are not limited thereto, and the amount of the ingredients may be determined within the range not negatively affecting the purpose and effect of the present disclosure.

The composition for external application to skin according to an exemplary embodiment of the present disclosure may be a pharmaceutical composition. The pharmaceutical composition may further comprise a pharmaceutical adjuvant such as an antiseptic, a stabilizer, a hydrating agent, an emulsification accelerator, a salt and/or buffer for control of osmotic pressure, etc. and other therapeutically useful substances. In an exemplary embodiment, the pharmaceutical composition may be a formulation for parenteral administration. The formulation for parenteral administration may be a formulation for rectal, topical, subcutaneous or transdermal administration. For example, the formulation may be an injection, a medicinal drip, an ointment, a lotion, a gel, a cream, a spray, a suspension, an emulsion, a suppository, a patch, etc., although not being limited thereto.

In an exemplary embodiment, the administration amount of the pharmaceutical composition will vary depending on the age, sex and body weight of a subject to be treated, the particular disease or pathological condition to be treated, the severity of the disease or pathological condition, administration route and discretion of a prescriber. The determination of the administration amount based on these factors is within the level of those skilled in the art. For example, the administration amount may be 1 mg/kg/day or more or 500 mg/kg/day or more, and 1 g/kg/day or less, 500 mg/kg/day or less or 100 mg/kg/day or less. However, the administration amount does not limit the scope of the present disclosure by any means.

MODE FOR INVENTION

Hereinafter, the present disclosure will be described in detail through examples, comparative examples and test examples. However, the following examples are for illustrative purposes only and it will be obvious to those of ordinary skill in the art that the scope of the present disclosure is not limited by the examples, comparative examples and test examples.

Example 1

An active substance carrier comprising a core-shell network structure according to an exemplary embodiment of the present disclosure was prepared as follows.

After weighing 0.5 wt % of zein in powder form based on the total weight of a composition and adding to a 70% alcohol aqueous solution, it was dispersed by stirring the mixture. Then, after weighing 0.5 wt % of pullulan dissolved in an aqueous phase of pH 7 or lower based on the total weight of the composition at room temperature, it was added drop by drop to the alcohol solution, and then dissolved by stirring the mixture. Also, after weighing 0.5 wt % of pectin in an aqueous phase based on the total weight of the composition, it was added to the solution. Finally, a core-shell network solution dissolved in an aqueous phase was obtained by evaporating the alcohol from the solution using an evaporator.

Example 2

A composition comprising an active substance-loaded core-shell network structure according to an exemplary embodiment of the present disclosure was prepared as follows.

After weighing 0.5 wt % of zein in powder form based on the total weight of a composition and adding to a 70% alcohol aqueous solution, it was dissolved by stirring the mixture. Then, after adding 1 wt % of red ginseng saponin (BioGF1K Complex™, Amorepacific) based on the total weight of the composition to the solution as an active substance, the mixture was dispersed by stirring sufficiently such that hydrophobic interaction occurred between the zein and the active substance. Then, after weighing 0.5 wt % of pullulan dissolved in an aqueous phase of pH 7 or lower based on the total weight of the composition at room temperature, it was added and dissolved by stirring the mixture. Then, after weighing 0.5 wt % of pectin in an aqueous phase based on the total weight of the composition, it was added to the solution. Finally, a core-shell network solution dissolved in an aqueous phase was obtained by evaporating the alcohol from the solution using an evaporator.

Comparative Example 1

An active substance carrier not comprising a network structure was prepared as follows as a comparative example of the present disclosure.

After weighing 0.5 wt % of zein in powder form based on the total weight of a composition and adding to a 70% alcohol aqueous solution, it was dispersed by stirring the mixture. Then, after weighing 0.5 wt % of pullulan dissolved in an aqueous phase of pH 7 or lower based on the total weight of the composition at room temperature, it was added drop by drop to the alcohol solution, and then dissolved by stirring the mixture. Finally, a core-shell solution dissolved in an aqueous phase was obtained by evaporating the alcohol from the solution using an evaporator.

Comparative Example 2

A composition comprising an active substance-loaded core-shell structure not comprising a network structure was prepared as follows as a comparative example of the present disclosure.

After weighing 0.5 wt % of zein in powder form based on the total weight of a composition and adding to a 70% alcohol aqueous solution, it was dissolved by stirring the mixture. Then, after adding 1 wt % of red ginseng saponin (BioGF1K Complex™, Amorepacific) based on the total weight of the composition to the solution as an active substance, the mixture was dispersed by stirring sufficiently such that hydrophobic interaction occurred between the zein and the active substance. Then, after weighing 0.5 wt % of pullulan dissolved in an aqueous phase of pH 7 or lower based on the total weight of the composition at room temperature, it was added and dissolved by stirring the mixture. Finally, a core-shell solution dissolved in an aqueous phase was obtained by evaporating the alcohol from the solution using an evaporator.

Test Example 1

The core-shell structures formed in the compositions of Comparative Example 1, Comparative Example 2, Example 1 and Example 2 were identified by scanning electron microscopy (SEM) and are shown in FIG. 2A, FIG. 2B, FIG. 3A and FIG. 3B, respectively.

Figure 2A:
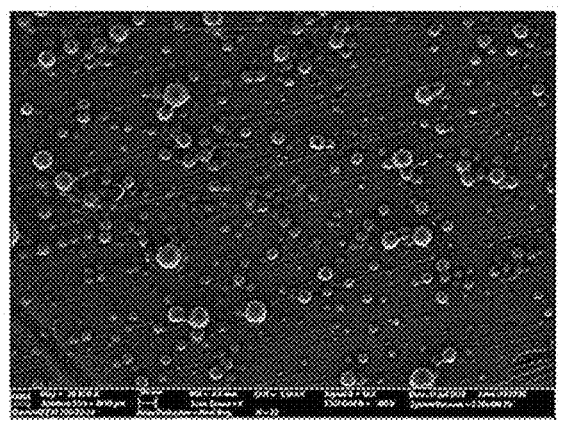
FIG. 2A shows an electron microscopic image of a comparative example (not comprising an active substance) with no core-shell network formed.
Figure 2B:
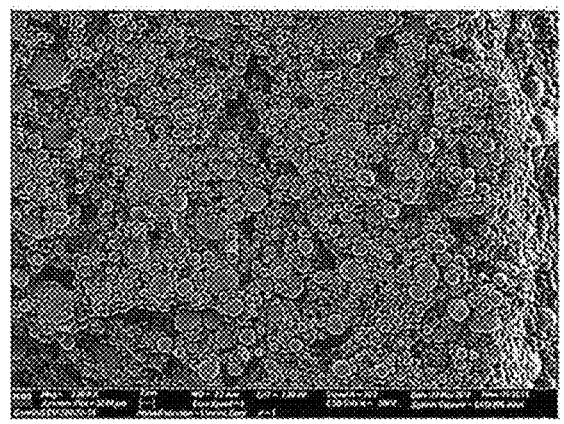
FIG. 2B shows an electron microscopic image of a comparative example (comprising an active substance) with no core-shell network formed.

For Comparative Example 1, although a core-shell structure was formed, the particles of the structure were distributed apart from each other (FIG. 2A). For Comparative Example 2, wherein the active substance was loaded, the distributed structure was collapsed and the particles were aggregated with each other (FIG. 2B).

Figure 3A:
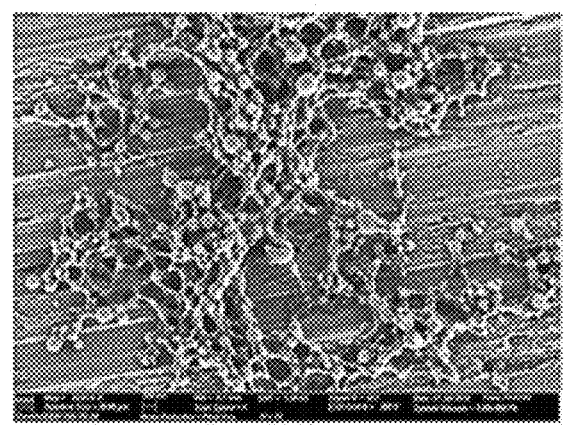
FIG. 3A shows an electron microscopic image confirming the formation of a core-shell network structure (not comprising an active substance) according to an exemplary embodiment of the present disclosure.

In contrast, for Example 1, a web-like network was formed between core-shell structures and supported the uniformed distributed particles in the solution (FIG. 3A). For Example 2, wherein the active substance was loaded, the particles with a size of 200-500 nm were interconnected with each other and distributed uniformly with regular distances (FIG. 3B).

Figure 3B:
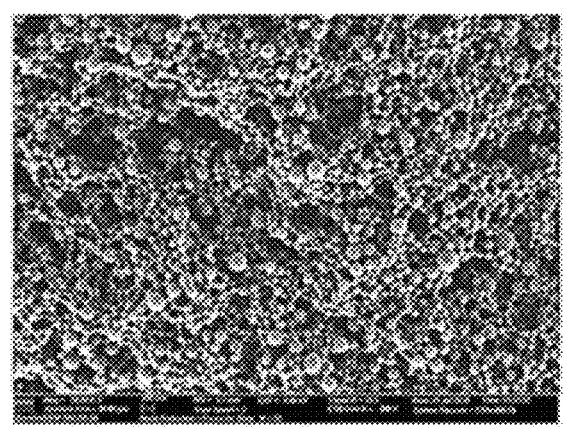
FIG. 3B shows an electron microscopic image confirming the formation of a core-shell network structure (comprising an active substance) according to an exemplary embodiment of the present disclosure.
Figure 4A:
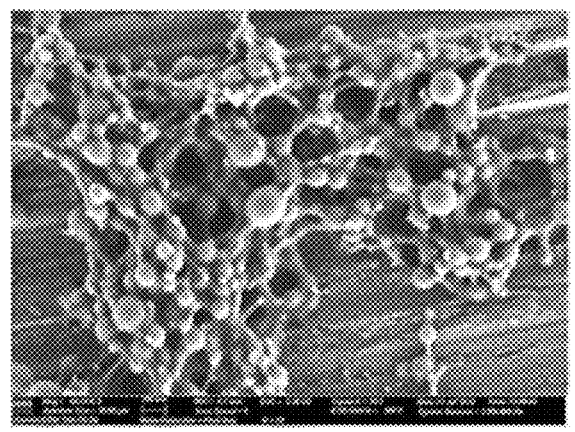
FIG. 4A shows an electron microscopic image, which is an enlarged image of FIG. 3A, confirming the formation of a core-shell network structure (not comprising an active substance) according to an exemplary embodiment of the present disclosure.
Figure 4B:
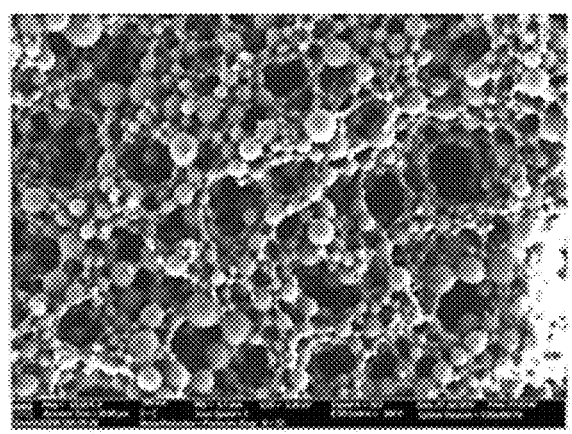
FIG. 4B shows an electron microscopic image, which is an enlarged image of FIG. 3B, confirming the formation of a core-shell network structure (comprising an active substance) according to an exemplary embodiment of the present disclosure.

FIG. 4A and FIG. 4B show enlarged images of the structures in the solutions of FIG. 3A and FIG. 3B. It can be seen that core-shell structures with a size of hundreds of nanometers are formed in the exemplary embodiments of the present disclosure and the particles are densely interconnected with each other and are distributed uniformly.

Figure 5:
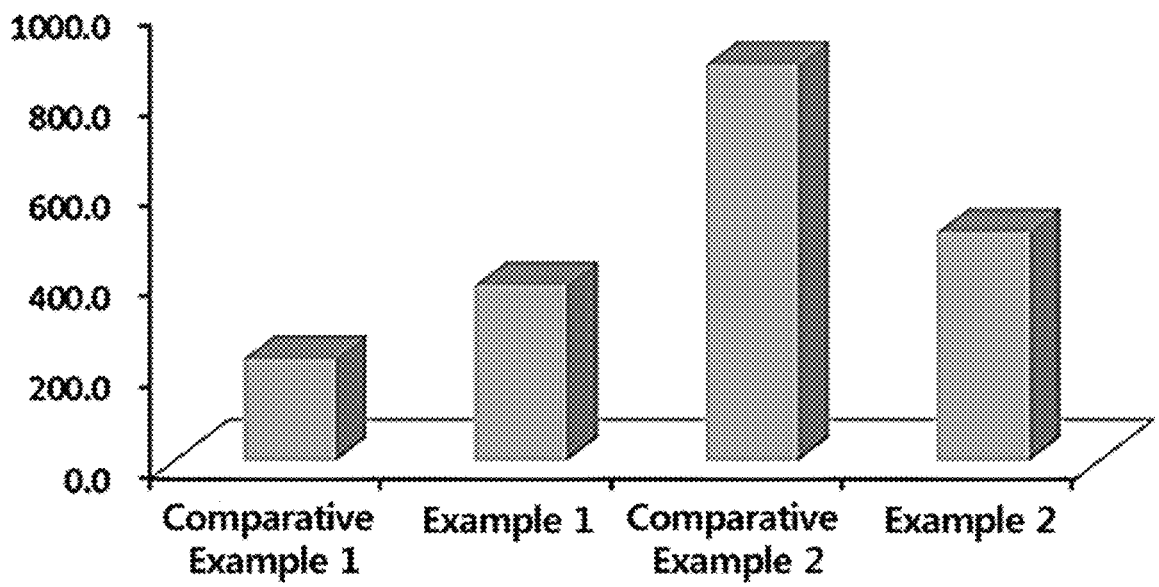
FIG. 5 shows a result of measuring the size of a core-shell particle in compositions of exemplary embodiments of the present disclosure and comparative examples.

FIG. 5 shows the hydrodynamic average particle size of the particles formed in the solutions of Comparative Examples 1-2 and Examples 1-2 measured using a dynamic light scattering instrument (Marven). For Comparative Example 2 with no interconnection between the core-shell particles, the volume was increased by about 4 times or more as compared to Comparative Example 1 when the active substance was loaded. In contrast, for Example 2, the change in size after the loading of the active substance was not significant, and the particle size was still about 500 nm or smaller. This means that, according to the present disclosure, the structure of the core-shell particles is maintained firmly because the particles are interconnected with each other.

Figure 6A:
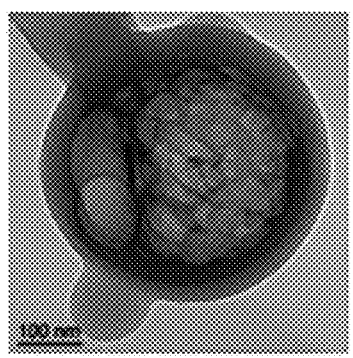
FIG. 6A shows that a core-shell particle in the form of a droplet is formed in a solution comprising a core-shell network structure according to an exemplary embodiment of the present disclosure.
Figure 6B:
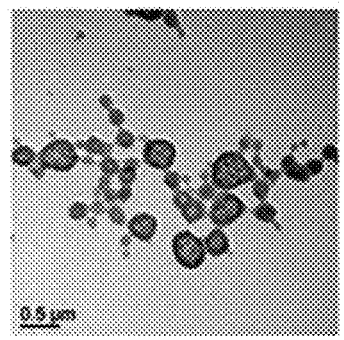
FIG. 6B shows that a core-shell particle in the form of a droplet is formed in a solution comprising a core-shell network structure according to an exemplary embodiment of the present disclosure, thereby forming a network structure, and is present in the solution in the form of an active substance carrier.

FIG. 6A and FIG. 6B show images obtained by dropping 5 μL of the solution of Example 1 on a carbon film 220 mesh copper (CF200-Cu)) TEM grid and imaging with a high-resolution transmission electron microscope (HRTEM (EDS), JEM-3010) after drying overnight. As shown in FIG. 6A and FIG. 6B, core-shell particles with a size of 100-300 nm were present in an aqueous phase in the form of droplets in Example 1 (FIG. 6A), and a network was formed between the core-shell particles (FIG. 6B).

Test Example 2

The following experiment was conducted in order to investigate whether the core-shell network structure according to an exemplary embodiment of the present disclosure serves as a carrier facilitating the transdermal absorption of an active substance.

First, a core-shell network solution (Example 3) was prepared in the same manner as in Example 2 except that, instead of the red ginseng saponin as the active substance, a hydrophobic fluorescent dye (Nile red, Sigma-Aldrich) was encapsulated at a concentration of 318.369 g/mol. The contents of zein, pullulan and pectin of Example 3 based on the total weight of the composition were 0.01 wt %, 0.02 wt % and 0.002 wt %, respectively.

Then, 200,000 human epidermal keratinocytes (Catalog No. C01510C, Gibco) were seeded onto an artificial skin culture vessel (Snapwell™, Corning) and cultured for 48 hours using a serum-free medium (Epilife®, Gibco). After removing the medium and adding a high-calcium medium (CnT-PR-3D, Cellntec), the cells were cultured additionally for 24 hours.

The cells were exposed to the air by removing the medium except for the part occupied by the cells. Subsequently, the cells were cultured for 14 days while replacing the medium once in 48 hours. On day 14, the test substance of Example 3 was coated on the surface of the prepared artificial skin, i.e., on the stratum corneum. After a night passed, the substance on the surface was removed as much as possible. After freezing using an OCT (Cryomatrix, Thermo Scientific) and slicing to a thickness of 10 μm, the frozen sections were imaged with a fluorescence microscope (BX53, Olympus, Japan) and a microscopic digital camera (DP72, Olympus, Japan). The thickness of the stratum corneum of the artificial skin was 10.73 μm on average. To compare the effect of the present disclosure, the stratum corneum of the skin was treated only with a hydrophobic fluorescent dye in Comparative Example 3, and the degree of penetration of the hydrophobic fluorescent dye was analyzed in the same manner.

Figure 7A:
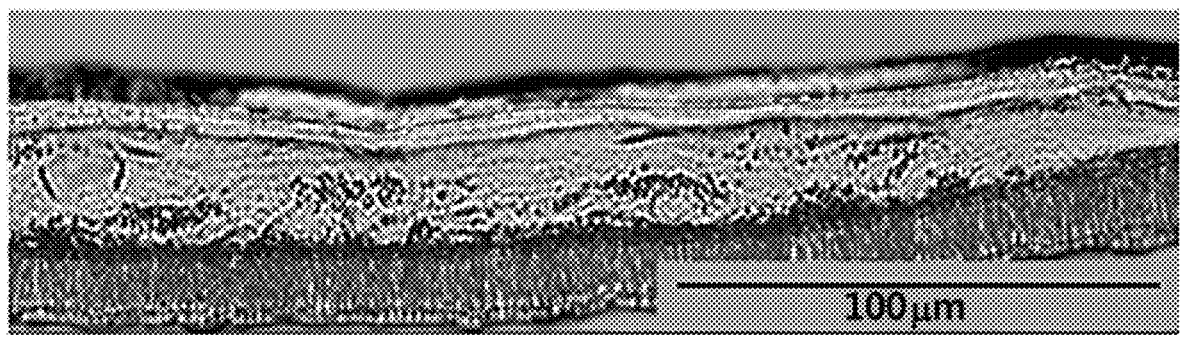
FIG. 7A shows a result of investigating the degree of transdermal penetration of a hydrophobic fluorescent dye alone as a comparative example of the present disclosure in Comparative Example 3.
Figure 7B:
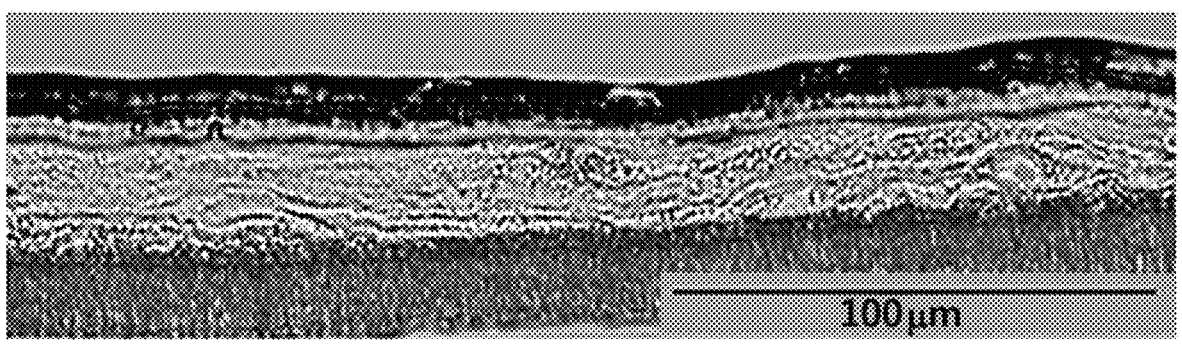
FIG. 7B shows a result of confirming that a core-shell network structure according to an exemplary embodiment of the present disclosure facilitates the transdermal penetration of a hydrophobic fluorescent dye in Example 3.

As a result, for Comparative Example 3 treated only with the hydrophobic fluorescent dye, the dye penetrated up to about 3.62 μm on average into the stratum corneum of the cultured artificial skin, whose average thickness was 10.73 μm (FIG. 7A). In contrast, for Example 3 according to an exemplary embodiment of the present disclosure, the dye penetrated up to about 10.51 μm on average (FIG. 7B). This means that the core-shell network structure according to an exemplary embodiment of the present disclosure serves as a carrier which facilitates the transdermal absorption of an active substance and allows penetration of the active substance into the stratum corneum of the skin.

Test Example 3

The following experiment was conducted in order to investigate the effect of the core-shell network structure according to an exemplary embodiment of the present disclosure as a carrier facilitating the transdermal absorption of an active substance.

First, a core-shell network solution was prepared in the same manner as in Example 1. The contents of zein, pullulan and pectin based on the total weight of the composition were 0.01 wt %, 0.02 wt % and 0.002 wt %, respectively. The prolamin protein zein of the core in the solution was tagged with the hydrophilic fluorescent dye Alexa Fluor® 594 (Thermo Fisher) at 819.85 g/mol through amide bonding using the Thermo Fisher protein labeling Kit® (Example 4). As a comparative example of the present disclosure, the same hydrophilic fluorescent dye Alexa Fluor® 594 (Thermo Fisher) was tagged for Comparative Example 1 (Comparative Example 4).

Figure 8A:
FIG. 8A shows the section of artificial skin as a control group (non-treated group) of the present disclosure.

Then, 200,000 human epidermal keratinocytes (Catalog No. C01510C, Gibco) were seeded onto an artificial skin culture vessel (Snapwell™, Corning) and cultured for 48 hours using a serum-free medium (Epilife®, Gibco). After removing the medium and adding a high-calcium medium (CnT-PR-3D, Cellntec), the cells were cultured additionally for 24 hours. The cells were exposed to the air by removing the medium except for the part occupied by the cells. Subsequently, the cells were cultured for 14 days while replacing the medium once in 48 hours. On day 14, the test substance of Example 4 or Comparative Example 4 was coated on the surface of the prepared artificial skin, i.e., on the stratum corneum. After 3 hours or a night passed, the substance on the surface was removed as much as possible. After freezing using an OCT (Cryomatrix, Thermo Scientific) and slicing to a thickness of 10 μm, the frozen sections were imaged with a fluorescence microscope (BX53, Olympus, Japan) and a microscopic digital camera (DP72, Olympus, Japan). The thickness of the stratum corneum of the artificial skin was 11.89 μm on average (FIG. 8A).

Figure 8B:
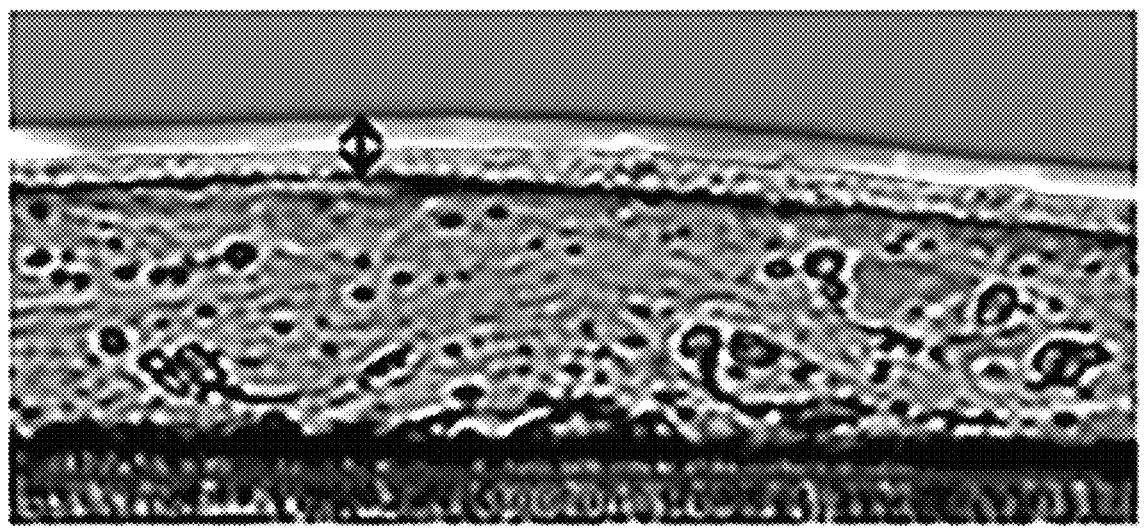
FIG. 8B shows an image obtained 3 hours after the application of Comparative Example 4 as a comparative example of the present disclosure onto the surface of artificial skin.
Figure 8C:
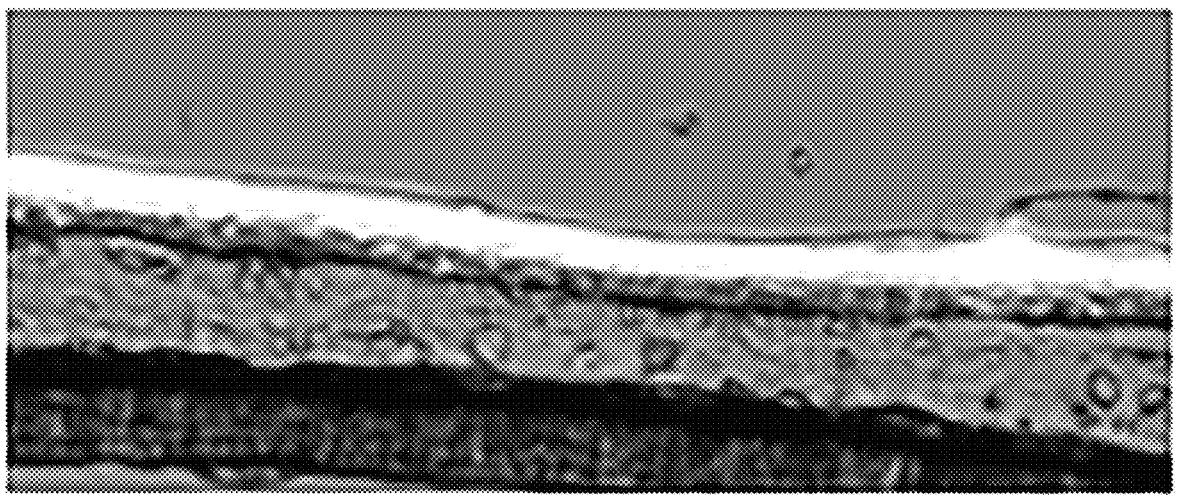
FIG. 8C shows an image obtained 3 hours after the application of a core-shell network structure of Example 4 according to an exemplary embodiment of the present disclosure onto the surface of artificial skin.
Figure 9A:
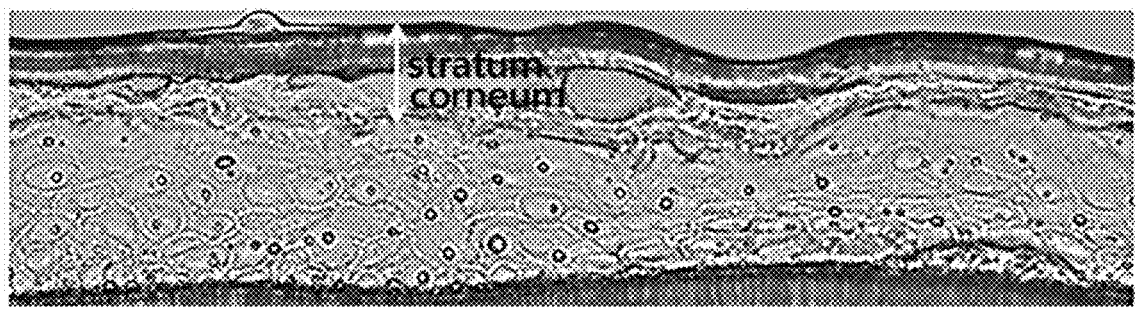
FIG. 9A shows an image obtained one day after the application of Comparative Example 4 as a comparative example of the present disclosure onto the surface of artificial skin.
Figure 9B:
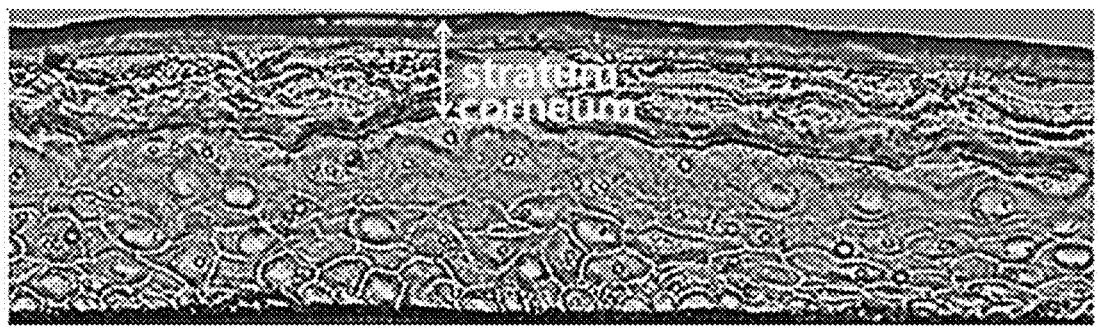
FIG. 9B shows an image obtained one day after the application of a core-shell network structure of Example 4 according to an exemplary embodiment of the present disclosure onto the surface of artificial skin.

FIG. 8B and FIG. 8C show microscopic images obtained 3 hours had passed and FIG. 9A and FIG. 9B show microscopic images obtained a night had passed. As shown in FIG. 9A, for Comparative Example 4, the dye penetrated up to about 5.37 μm on average from the surface of the skin. In contrast, as shown in FIG. 9B, for Example 4 according to an exemplary embodiment of the present disclosure, the dye penetrated up to about 10.98 μm on average. This means that the structure according to the present disclosure, which comprises pectin between core-shell particles, has remarkably enhanced effect of transdermally absorbing an active substance and allows penetration of the active substance into the stratum granulosum after passing through the stratum corneum of the skin.

The present disclosure may provide the following exemplary embodiments.

A first exemplary embodiment may provide an active substance carrier comprising a core-shell network structure comprising a core-shell particle consisting of a core comprising prolamin; and a shell comprising pullulan and pectin, wherein the pullulan comprised in the shell surrounds the core and the pectin is located in the outermost layer of the shell, so that a network is formed between the core-shell particles.

A second exemplary embodiment may provide the active substance carrier according to the first exemplary embodiment, wherein the prolamin comprises one or more selected from a group consisting of zein, hordein, secalin, kafirin, gliadin, oryzin and avenin.

A third exemplary embodiment may provide the active substance carrier according to one or more of the first exemplary embodiment and the second exemplary embodiment, wherein the core-shell network structure comprises:
0.001-7.5 wt % of prolamin;
0.001-12.5 wt % of pullulan; and
0.001-10 wt % of pectin
based on the total weight of the structure.

A fourth exemplary embodiment may provide the active substance carrier according to one or more of the first to third exemplary embodiments, wherein the core-shell particle has an average particle size which is greater than 100 nm and equal to or smaller than 600 nm.

A fifth exemplary embodiment may provide the active substance carrier according to one or more of the first to fourth exemplary embodiments, wherein the core-shell network structure is a carrier for facilitating the transdermal absorption of an active substance.

A sixth exemplary embodiment may provide the active substance carrier according to one or more of the first to fifth exemplary embodiments, wherein the active substance is water-insoluble or poorly water-soluble.

A seventh exemplary embodiment may provide a composition for external application to skin, which comprises the active substance carrier according to one or more of the first to sixth exemplary embodiments and an active substance.

An eighth exemplary embodiment may provide the composition for external application to skin according to the seventh exemplary embodiment, wherein the composition comprises 0.01 wt %-10 wt % of an active substance based on the total weight of the composition.

A ninth exemplary embodiment may provide the composition for external application to skin according to one or more of the seventh and eighth exemplary embodiments, wherein the weight ratio of the active substance carrier with respect to the total weight of the active substance is 0.001-10:0.02-22.

A tenth exemplary embodiment may provide the composition for external application to skin according to one or more of the seventh to ninth exemplary embodiments, wherein the active substance is encapsulated in the prolamin comprised in the core of the core-shell network structure.

An eleventh exemplary embodiment may provide the composition for external application to skin according to one or more of the seventh to tenth exemplary embodiments, wherein the prolamin of the core forms a brick-like layered structure around the active substance.

A twelfth exemplary embodiment may provide the composition for external application to skin according to one or more of the seventh to eleventh exemplary embodiments, wherein the composition is a cosmetic composition.

A thirteenth exemplary embodiment may provide the composition for external application to skin according to one or more of the seventh to twelfth exemplary embodiments, wherein the composition is a pharmaceutical composition.

A fourteenth exemplary embodiment may provide a method for transdermal delivery of an active substance, which comprises administering an effective amounts of the active substance carrier according to the first to thirteenth exemplary embodiment with an active substance loaded to a subject in need thereof.

A fifteenth exemplary embodiment may provide the method according to the first to fourteenth exemplary embodiments, wherein the prolamin is one or more selected from a group consisting of zein, hordein, secalin, kafirin, gliadin, oryzin and avenin.

A sixteenth exemplary embodiment may provide the method according to the first to fifteenth exemplary embodiments, wherein the core-shell network structure comprises: 0.001-7.5 wt % of prolamin; 0.001-12.5 wt % of pullulan; and 0.001-10 wt % of pectin, based on the total weight of the structure.

A seventeenth exemplary embodiment may provide the method according to the first to sixteenth exemplary embodiments, wherein the core-shell particle has an average particle size which is greater than 100 nm and equal to or smaller than 600 nm.

An eighteenth exemplary embodiment may provide the method according to the first to seventeenth exemplary embodiments, wherein the active substance is water-insoluble or poorly water-soluble.

A nineteenth exemplary embodiment may provide the method according to the first to eighteenth exemplary embodiments, wherein the weight ratio of the active substance carrier with respect to the total weight of the active substance is 0.001-10:0.02-22.

A twentieth exemplary embodiment may provide the method according to the first to nineteenth exemplary embodiments, wherein the active substance is encapsulated in the prolamin comprised in the core of the core-shell network structure.

The invention claimed is:

1. A method for transdermal delivery of an active substance, comprising administering an effective amount of an active substance carrier with an active substance loaded to a subject in need thereof,
the active substance carrier comprising a core-shell network structure comprising a core-shell particle consisting of a core comprising prolamin; and a shell comprising pullulan and pectin, wherein the pullulan comprised in the shell surrounds the core and the pectin is located in the outermost layer of the shell, so that a network is formed between the core-shell particles,
wherein the prolamin is zein,
wherein the core-shell network structure comprises:
0.001-7.5 wt % of prolamin;
0.001-12.5 wt % of pullulan; and
0.001-10 wt % of pectin;
based on a total weight of the structure,
wherein the core-shell particle has an average particle size which is greater than 100 nm and equal to or smaller than 600 nm, and
wherein a weight ratio of the active substance carrier with respect to a total weight of the active substance is 0.001-10:0.02-22.

2. The method according to claim 1, wherein the active substance is water-insoluble or poorly water-soluble.

3. The method according to claim 1, wherein the active substance is encapsulated in the prolamin comprised in the core of the core-shell network structure.

* * * * *